US012362036B2

(12) United States Patent
Jumper et al.

(10) Patent No.: US 12,362,036 B2
(45) Date of Patent: Jul. 15, 2025

(54) PROTEIN STRUCTURE PREDICTION USING GEOMETRIC ATTENTION NEURAL NETWORKS

(71) Applicant: DeepMind Technologies Limited, London (GB)

(72) Inventors: John Jumper, London (GB); Andrew W. Senior, London (GB); Richard Andrew Evans, London (GB); Stephan Gouws, London (GB); Alexander Bridgland, London (GB)

(73) Assignee: DeepMind Technologies Limited, London (GB)

( * ) Notice: Subject to any disclaimer, the term of this patent is extended or adjusted under 35 U.S.C. 154(b) by 1158 days.

(21) Appl. No.: 16/701,070

(22) Filed: Dec. 2, 2019

(65) Prior Publication Data

US 2021/0398606 A1    Dec. 23, 2021

Related U.S. Application Data

(60) Provisional application No. 62/774,071, filed on Nov. 30, 2018.

(51) Int. Cl.
*G16B 15/20* (2019.01)
*G16C 20/30* (2019.01)
(Continued)

(52) U.S. Cl.
CPC ............. *G16B 15/20* (2019.02); *G16C 20/30* (2019.02); *G16C 20/60* (2019.02); *G16C 20/70* (2019.02); *G16C 20/90* (2019.02)

(58) Field of Classification Search
CPC ........ G16B 15/20; G16B 40/00; G16C 20/30; G16C 20/60; G16C 20/70; G16C 20/90; G06N 3/045; G06N 3/048; G06N 3/08
See application file for complete search history.

(56) References Cited

U.S. PATENT DOCUMENTS

| 5,958,784 A | 9/1999 | Benner |
| 2008/0215301 A1 | 9/2008 | Eyal et al. |

(Continued)

FOREIGN PATENT DOCUMENTS

| CN | 101294970 | 10/2008 |
| CN | 101647022 | 2/2010 |

(Continued)

OTHER PUBLICATIONS

Dorn, M. Three-dimensional protein structure prediction: methods and computational strategies. Computational Biology and Chemistry 53: 251-276. (Year: 2014).*

(Continued)

*Primary Examiner* — Olivia M. Wise
*Assistant Examiner* — Robert J. Kallal
(74) *Attorney, Agent, or Firm* — Fish & Richardson P.C.

(57) ABSTRACT

Methods, systems, and apparatus, including computer programs encoded on a computer storage medium, for determining a predicted structure of a protein that is specified by an amino acid sequence. In one aspect, a method comprises: obtaining an initial embedding and initial values of structure parameters for each amino acid in the amino acid sequence, wherein the structure parameters for each amino acid comprise location parameters that specify a predicted three-dimensional spatial location of the amino acid in the structure of the protein; and processing a network input comprising the initial embedding and the initial values of the structure parameters for each amino acid in the amino acid sequence using a folding neural network to generate a network output comprising final values of the structure parameters for each amino acid in the amino acid sequence.

20 Claims, 4 Drawing Sheets

(51) Int. Cl.
   *G16C 20/60* (2019.01)
   *G16C 20/70* (2019.01)
   *G16C 20/90* (2019.01)

(56) References Cited

U.S. PATENT DOCUMENTS

| | | |
|---|---|---|
| 2013/0303383 A1 | 11/2013 | Sander et al. |
| 2013/0304432 A1 | 11/2013 | Sander et al. |
| 2017/0249420 A1 | 8/2017 | Saladi et al. |
| 2017/0316147 A1 | 11/2017 | Gao et al. |

FOREIGN PATENT DOCUMENTS

| | | |
|---|---|---|
| CN | 101794351 | 8/2010 |
| CN | 105468934 | 4/2016 |
| CN | 105740646 | 7/2016 |
| CN | 106503484 | 3/2017 |
| CN | 107330512 | 11/2017 |
| CN | 107506613 | 12/2017 |
| CN | 107622182 | 1/2018 |
| EP | 1482433 | 12/2004 |
| JP | 2004258814 | 9/2004 |
| JP | 2022130054 | 9/2022 |
| WO | WO 0214875 | 2/2002 |
| WO | WO 2017062382 | 4/2017 |

OTHER PUBLICATIONS

Du, M. Empirical study of deep neural network architectures for protein secondary structure prediction. Master's Thesis, University of Missouri, 44 pgs. (Year: 2007).*
Diamond, R. On the multiple simultaneous superposition of molecular structures by rigid body transformations. Protein Science 1: 1279-1287. (Year: 1992).*
Benros, C. Accessing a novel approach for predicting local 3D protein structures from sequence. Proteins: Structure, Function, and Bioinformatics 62(4): 865-880. (Year: 2006).*
Hanson AJ. Quaternion maps of global protein structure. Journal of Molecular Graphics and Modelling 38: 256-278. (Year: 2012).*
Drori I. High quality prediction of protein Q8 secondary structure by diverse neural network architectures. arXiv 1811.07143. 10 pgs. (Year: 2018).*
Pollastri G. Improving the prediction of protein secondary structure in three and eight classes using recurrent neural networks and profiles. Proteins: Structure, Function, and Genetics 47: 228-235. (Year: 2002).*
Bohr et al., "A novel approach to prediction of the 3-dimensional structures of protein backbones by neural networks," FEBS Letters, Feb. 1990, 261(1):43-46.
Bohr J et al., "Protein Structures from Distance Inequalities," Journal of Molecular Biology, Jun. 1993, 231(3):861-869.
Boomsma et al., "A generative, probabilistic model of local protein structure," PNAS, Jan. 2008, 105(26):8932-8937.
Derevyanko et al., "Deep convolutional networks for quality assessment of protein folds," Bioinformatics, Jan. 2018, 34(23):4046-4053.
Fan et al., "Virtual Ligand Screening Against Comparative Protein Structure Models," Methods in Molecular Biology, Nov. 2012, 819:105-126.
Feig et al., "Computational protein structure refinement: almost there, yet still so far to go: Computational protein structure refinement," WIREs Computational Molecular Science, Mar. 2017, 7(3):1-24.
Fredholm et al., "A Novel Approach to Prediction of the 3-Dimensional Structures of Protein Backbones by Neural Networks," Advances in Neural Information Processing Systems 3, Dec. 1990, pp. 523-529.
Kukic et al., "Toward an accurate prediction of inter residue distances in proteins using 2D recursive neural networks," BMC Bioinformatics, Jan. 2014, 15(6): 15 pages.

Office Action in Canadian Appln. No. 3,110,200, dated Feb. 9, 2022, 5 pages.
Office Action in Canadian Appln. No. 3,110,242, dated Feb. 9, 2022, 5 pages.
Office Action in Canadian Appln. No. 3,110,395, dated Feb. 9, 2022, 5 pages.
Office Action in Indian Appln. No. 202127003862, dated Jan. 7, 2022, 9 pages.
Reczko et al., "Recurrent Neural Networks for Protein Distance Matrix Prediction," IOS Press, Dec. 1994, pp. 88-97.
Sali et al., "Comparative Protein Modelling by Satisfaction of Spatial Restraints," J. Mol. Biol., Dec. 1993, 234(3):779-815.
Uziela et al., "ProQ3D: improved model quality assessments using deep learning," Bioinformatics, Jan. 2017, 33(10):1578-1580.
Wang et al., "Accurate De Novo Prediction of Protein Contact Map by Ultra-Deep Learning Model," PLOS Computational Biology, Jan. 2017, 13(1):e1005324.
Zhao et al., "A Position-Specific Distance-Dependent Statistical Potential for Protein Structure and Functional Study," Structure, Apr. 2012, 20(6):1118-1126.
Zhu et al., "Protein threading using residue co-variation and deep learning," Bioinformatics, Jun. 2018, 34(13):1263-1273.
Defay et al., "Evaluation of Current Techniques for Ab Initio Protein Structure Prediction," Proteins: Structure, Function, and Genetics, 1995, 23:431-445.
Knighton et al., "Crystal Structure of the Catalytic Subunit of Cyclic Adenosine Monophosphate-Dependent Protein Kinase," Science, Jul. 1991, 253:5018:407-414.
Prodromou et al., "Identification and Structural Characterization of the ATP/ADP-Binding Site in the Hsp90 Molecular Chaperone," Cell, Jul. 1991, 90:65-75.
Thornton et al., "Prediction of Progress at Least," Nature, Nov. 1991, 354:105-106.
AlQuraishi, "End-to-end differentiable learning of protein structure," bioRxiv, Feb. 2018, 36 pages.
Ba et al., "Layer Normalization," https://arxiv.org/abs/1607.06450, Jul. 2016, 14 pages.
Bahdanau et al., "Neural machine translation by jointly learning to align and translate," https://arxiv.org/abs/1409.0473v4, Dec. 2014, 15 pages.
Bengio et al., "Can active memory replace attention?" In Advances in Neural Information Processing Systems, (NIPS), Dec. 2016, 9 pages, First author is Kaiser.
Britz et al., "Massive exploration of neural machine translation architectures," https://arxiv.org/abs/1703.03906v2, Mar. 2017, 9 pages.
Cheng et al., "Long short-term memory-networks for machine reading," arXiv preprint arXiv:1601.06733, Sep. 2016, 11 pages.
Cho et al., "Learning Phrase Representations using RNN Encoder-Decoder for Statistical Machine Translation," https://arxiv.org/abs/1406.1078v3, last revised Sep. 2014, 15 pages.
Chollet, "Xception: Deep Learning with Depthwise Separable Convolutions," https://arxiv.org/abs/1610.02357v2, Oct. 2016, 14 pages.
Chung et al., "Empirical Evaluation of Gated Recurrent Neural Networks on Sequence Modeling," https://arxiv.org/abs/1412.3555, Dec. 2014, 9 pages.
Gehring et al., "Convolutional sequence to sequence learning," arXiv preprint arXiv:1705.03122v2, Jul. 2017, 15 pages.
Graves, "Generating Sequences With Recurrent Neural Networks," https://arxiv.org/abs/1308.0850v2, Aug. 2013, 43 pages.
He et al., "Deep Residual Learning for Image Recognition," Proceedings of the IEEE Conference on Computer Vision and Pattern Recognition, 2016, 770-778.
Hochreiter et al., "Gradient flow in recurrent nets: the difficulty of learning long-term dependencies," bioinf.jku.at, 2001, 15 pages.
Hochreiter et al., "Long short-term memory," Neural Computation, Nov. 1997, 9(8):1735-1780, 32 pages.
Ingraham et al., "Learning protein structure with a differentiable simulator," International Conference on Learning Representations, Feb. 2019, 24 pages.
Jozefowicz et al., "Exploring the Limits of Language Modeling," https://arxiv.org/abs/1602.02410, Feb. 2016, 11 pages.

(56) References Cited

OTHER PUBLICATIONS

Kaiser et al., "Neural GPUs learn algorithms," In International Conference on Learning Representations (ICLR), Mar. 2016, 9 pages.

Kalchbrenner et al., "Neural machine translation in linear time," arXiv preprint arXiv:1610.10099v2, Mar. 2017, 9 pages.

Kim et al., "Structured attention networks," https://arxiv.org/abs/1702.00887, Feb. 2017, 21 pages.

Kingma et al., "Adam: A Method for Stochastic Optimization," https://arxiv.org/abs/1412.6980v8, Jul. 2015, 15 pages.

Kuchaiev et al., "Factorization tricks for LSTM networks," https://arxiv.org/abs/1703.10722v2, May 2017, 5 pages.

Lin et al., "A Structured Self-attentive Sentence Embedding," https://arxiv.org/abs/1703.03130, Mar. 2017.

Luong et al., "Effective approaches to attention based neural machine translation," arXiv preprint arXiv:1508.04025, Sep. 2015, 11 pages.

Mariani et al., "lDDT: a local superposition-free score for comparing protein structures and models using distance difference tests," Bioinformatics, Aug. 2013, 29(21):2722-2728.

Moré et al., "Distance geometry optimization for protein structures," Journal of Global Optimization, Aug. 1999, 15(3):219-234.

Parikh et al., "A Decomposable Attention Model for Natural Language Inference," Proceedings of the 2016 Conference on Empirical Methods in Natural Language Processing, Nov. 2016, 2249-2255.

Paulus et al., "A Deep Reinforced Model for Abstractive Summarization," https://arxiv.org/abs/1705.04304, last revised 2017, 12 page.

Press et al., "Using the Output Embedding to Improve Language Models," https://arxiv.org/abs/1608.05859v2, Nov. 2016, 11 pages.

Sennrich et al., "Neural Machine Translation of Rare Words with Subword Units," https://arxiv.org/abs/1508.07909v1, Aug. 2015, 11 pages.

Shazeer et al., "Outrageously Large Neural Networks: The Sparsely-Gated Mixture-of-Experts Layer," https://arxiv.org/abs/1701.06538, Jan. 2017, 19 pages.

Srivastava et al., "Dropout: a simple way to prevent neural networks from overfitting," Journal of Machine Learning Research, Jun. 2014, 15(1):1929-1958.

Sukhbaatar et al., "End-to-end memory networks," Advances in Neural Information Processing Systems, Jan. 2015, 9 pages.

Sutskever et al., "Sequence to sequence learning with neural networks," In Advances in Neural Information Processing Systems, pp. 3104-3112, 2014, 9 pages.

Szegedy et al., "Rethinking the inception architecture for computer vision," https://arxiv.org/abs/1512.00567, Dec. 2015, 10 pages.

Vaswani et al., "Attention Is All You Need," 31st Conference on Neural Information Processing Systems (NIPS 2017), Jun. 2017, 11 pages.

Wikipedia, "Quaternions and spatial rotation," Wikipedia, retrieved from the internet on Dec. 10, 2019 at URL <https://en.wikipedia.org/wiki/Quaternions_and_spatial_rotation>, 13 pages.

Wu et al., "Google's Neural Machine Translation System: Bridging the Gap between Human and Machine Translation," https://arxiv.org/abs/1609.08144, Oct. 2016, 23 pages.

Zhou et al., "Deep recurrent models with fast-forward connections for neural machine translation," Transactions of the Association for Computational Linguistics, Jul. 2016, 4: 371-383.

PCT International Preliminary Report on Patentability in Appln. No. PCT/EP2019/074670, dated Mar. 23, 2021, 17 pages.

PCT International Preliminary Report on Patentability in Appln. No. PCT/EP2019/074674, dated Mar. 23, 2021, 16 pages.

PCT International Preliminary Report on Patentability in Appln. No. PCT/EP2019/074676, dated Mar. 23, 2021, 16 pages.

Decision to Grant Patent in Japanese Appln. No. 2022-130054, dated Oct. 23, 2023, 5 pages (with English translation).

Office Action in Japanese Appln. No. 2022-130054, dated Jul. 10, 2023, 6 pages (with English translation).

Sadanandan et al., "Automated training of deep convolutional neural networks for cell segmentation," Scientific reports, 2017, 7.1:7860.

Xue et al., "Real-value prediction of backbone torsion angles," Proteins: Structure, Function, and Bioinformatics, 2008, 72.1:427-433.

Notice of Allowance in Chinese Appln. No. 201980054190.6, dated May 15, 2024, 6 pages (with English translation).

Office Action in Chinese Appln. No. 201980054171.3, dated May 17, 2024, 14 pages (with English translation).

Extended Search Report in European Appln. No. 24180923.5, dated Sep. 12, 2024, 17 pages.

Ferreira, Leonardo G., et al. "Molecular docking and structure-based drug design strategies." Molecules 20.7 (2015): 13384-13421. (Year: 2015).

Qian, N., 1999. On the momentum term in gradient descent learning algorithms. Neural networks, 12(1), pp. 145-151. (Year: 1999).

Rana, P. S., Sharma, H., Bhattacharya, M. and Shukla, A., 2015. Quality assessment of modeled protein structure using physicochemical properties. Journal of bioinformatics and computational biology, 13(02): 1550005, pp. 1-16. (Year: 2015).

Al-Lazikani et al., "Protein structure prediction," Current Opinion in Chemical Biology, 2001, 5:51-56.

Deng et al., "Protein Structure Prediction," Int. J. Mod. Phys. B, Jul. 2018, 32(18):18 pages.

Office Action in Chinese Appln. No. 201980054143.1, dated Dec. 19, 2023, 29 pages (with English translation).

Office Action in Chinese Appln. No. 201980054171.3, dated Dec. 28, 2023, 34 pages (with English translation).

Wang et al., "New Deep Neural Networks for Protein Model Evaluation," 2017 International Conference on Tools with Artificial Intelligence, Nov. 6, 2017, pp. 309-313.

Gao, Y., Wang, S., Deng, M. and Xu, J., Jan. 17, 2018. RaptorX-Angle: real-value prediction of protein backbone dihedral angles through a hybrid method of clustering and deep learning. BMC bioinformatics, 19, pp. 73-84. (Year: 2018).

\* cited by examiner

PROTEIN STRUCTURE PREDICTION USING GEOMETRIC ATTENTION NEURAL NETWORKS

CLAIM OF PRIORITY

This application claims priority to U.S. Provisional Patent Application No. 62/774,071, filed Nov. 30, 2018, the contents of which are incorporated here by reference in their entirety.

BACKGROUND

This specification relates to predicting protein structures.

A protein is specified by a sequence of amino acids. An amino acid is an organic compound which includes an amino functional group and a carboxyl functional group, as well as a side-chain (i.e., group of atoms) that is specific to the amino acid. Protein folding refers to a physical process by which a sequence of amino acids folds into a three-dimensional configuration. The structure of a protein defines the three-dimensional configuration of the atoms in the amino acid sequence of the protein after the protein undergoes protein folding. When in a sequence linked by peptide bonds, the amino acids may be referred to as amino acid residues.

Predictions can be made using machine learning models. Machine learning models receive an input and generate an output, e.g., a predicted output, based on the received input. Some machine learning models are parametric models and generate the output based on the received input and on values of the parameters of the model. The structure of a protein may be predicted based on the amino acid sequence that specifies the protein.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system implemented as computer programs on one or more computers in one or more locations that performs protein structure prediction.

In a first aspect there is provided a method performed by one or more data processing apparatus for determining a predicted structure of a protein that is specified by an amino acid sequence. The method may include obtaining an initial embedding and initial values of structure parameters for each amino acid in the amino acid sequence. The structure parameters for each amino acid may include location parameters that specify a predicted three-dimensional spatial location of the amino acid in the structure of the protein (e.g. an alpha or beta carbon atom location). The method may further include processing a network input including the initial embedding and the initial values of the structure parameters for each amino acid in the amino acid sequence using a folding neural network to generate a network output that includes final values of the structure parameters for each amino acid in the amino acid sequence. The folding neural network may include a set of update blocks. Each update block may include a set of neural network layers. Each update block may configured to receive an update block input including a current embedding and current values of the structure parameters for each amino acid in the amino acid sequence. Each update block may be further configured to process the update block input to update the current embedding and the current values of the structure parameters for each amino acid in the amino acid sequence. The final values of the structure parameters for each amino acid in the amino acid sequence collectively characterize the predicted structure of the protein.

In some implementations, this approach avoids the need to explicitly require chain continuity for the predicted folded structure. This in turn facilitates all parts of the protein to fold in parallel with large updates, which helps to increase speed of folding by orders of magnitude. The structure parameters for each amino acid may include rotation parameters that specify a predicted spatial orientation of the amino acid in the structure of the protein, e.g., defining a 3×3 rotation matrix.

An update block may include a geometric attention block and a folding block. The geometric attention block may update the current embedding for each amino acid, e.g., using a geometric self-attention operation which determines an attention weight between the embedding and each of one or more other selected embeddings. The attention weights may depend on the current embeddings and on the current values of the structure parameters. This helps the folding neural network reason about the 3D geometry of the amino acids in the protein structure, in particular, in a manner which is invariant to rotations and translations of the overall protein structure. In some implementations, the folding block updates the current values of the structure parameters using the updated embeddings.

In some implementations, updating the current embedding for a given amino acid in the amino acid sequence therefore includes determining an attention weight for each amino acid in the amino acid sequence. This may involve generating a three-dimensional (geometric) query embedding of the given amino acid based on the current embedding of the given amino acid, i.e., a query embedding that is three dimensional; generating, for each amino acid in the amino acid sequence, a three-dimensional (geometric) key embedding of the amino acid based on the current embedding of the amino acid; and determining the attention weight for each amino acid in the amino acid sequence based the three-dimensional key embedding of the amino acid and the three-dimensional query embedding of the given amino acid, e.g., based on (at least in part) a metric of a difference between these. The current embedding of the given amino acid may be updated using the attention weights, more particularly, using a (3D) attention weighted combination of (3D) value embeddings based on the current embeddings.

In some implementations, generating the three-dimensional query embedding includes processing the current embedding of the given amino acid using a linear neural network layer that generates a three-dimensional output, and applying a rotation operation and a translation operation to the three-dimensional output of the linear neural network layer. The three-dimensional key embedding may be generated similarly. The rotation operation may be specified by the current values of the rotation parameters for the given amino acid and the translation operation may be specified by the current values of the location parameters for the given amino acid.

In some implementations, updating the current embedding of a given amino acid includes generating, for each amino acid in the amino acid sequence, a three-dimensional value embedding of the amino acid based on the current embedding of the amino acid, determining a weighted linear combination of the three-dimensional value embeddings of the amino acids using the attention weights, generating a geometric return embedding by applying a rotation operation and a translation operation to the weighted linear combination, and updating the current embedding of the given amino acid based on the geometric return embedding. The rotation operation may invert a rotation operation specified by the current values of the rotation parameters for the given amino acid; the translation operation may be specified by a negative of the current values of the location parameters for the amino acid.

In some implementations, updating the current values of the structure parameters for each amino acid in the amino acid sequence includes, for each amino acid, determining updated values of the location parameters for the amino acid as a sum of the current values of the location parameters for the amino acid and a linear projection of the updated embedding of the amino acid. The updating may further include determining updated values of the rotation parameters for the amino acid as a composition of: (i) a rotation operation specified by the current values of the rotation parameters for the amino acid, and (ii) and a rotation operation specified by a quaternion with real part 1 and imaginary part specified by a linear projection of the updated embedding of the amino acid.

In a second aspect there is provided a system including: one or more computers; and one or more storage devices communicatively coupled to the one or more computers, where the one or more storage devices store instructions that, when executed by the one or more computers, cause the one or more computers to perform operations including the operations of the method of the first aspect.

In a third aspect there are provided one or more non-transitory computer storage media storing instructions that, when executed by one or more computers, cause the one or more computers to perform operations including the operations of the method of the first aspect.

Particular embodiments of the subject matter described in this specification can be implemented so as to realize one or more of the following advantages.

The system described in this specification can predict the structure of a protein by a single forward pass through a neural network, which may take less than one second. In contrast, some conventional systems predict the structure of a protein by an extended search process through the space of possible protein structures to optimize a scalar score function, e.g., using simulated annealing or gradient descent techniques. Such a search process may require millions of search iterations and consume hundreds of central processing unit (CPU) hours. Predicting protein structures by a single forward pass through a neural network may enable the system described in this specification to consume fewer computational resources (e.g., memory and computing power) than systems that predict protein structures by an iterative search process. Moreover, the system described in this specification can (in some cases) predict protein structures with an accuracy comparable to or higher than that of more computationally intensive systems.

The system described in this specification can predict a protein structure by repeatedly updating an initial (e.g., default) protein structure by updating structure parameters defining the spatial locations and rotations (i.e., orientations) of the amino acids in the protein structure. In contrast to some conventional systems, the system described in this specification does not explicitly require chain continuity of the individual amino acids of the protein on each update, but rather implicitly learns to generate predicted structures having chain continuity. This allows all parts of the protein to fold in parallel with large updates, which can enable the system to generate predicted structures more accurately than it otherwise would.

The system described in this specification may predict protein structures using operations that explicitly reasons about the 3-D geometry of the amino acids in the protein structure, while being invariant to global rotations and translations of the protein structure. For example, applying the same global rotation and translation operation to the initial protein structure provided to the system may cause the system to generate a predicted structure that is globally rotated and translated in the same way. Therefore, global rotation and translation operations applied to the initial protein structure would not affect the prediction accuracy of the system. The rotational and translational invariance of the representations generated by the system facilitates training, e.g., because the system automatically learns to generalize across all rotations and translations of protein structures.

The structure of a protein determines the biological function of the protein. Therefore, determining protein structures may facilitate understanding life processes (e.g., including the mechanisms of many diseases) and designing proteins (e.g., as drugs, or as enzymes for industrial processes). For example, which molecules (e.g., drugs) will bind to a protein (and where the binding will occur) depends on the structure of the protein. Since the effectiveness of drugs can be influenced by the degree to which they bind to proteins (e.g., in the blood), determining the structures of different proteins may be an important aspect of drug development. However, determining protein structures using physical experiments (e.g., by x-ray crystallography) can be time-consuming and very expensive. Therefore, the system described in this specification may facilitate areas of biochemical research and engineering which involve proteins (e.g., drug development).

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a protein folding neural network system for predicting the structure of a protein, that is, for predicting the three-dimensional configuration of the sequence of amino acids in the protein after the protein undergoes protein folding. The predicted structure of the protein may be defined by a set of structure parameters that define a spatial location and a rotation of each amino acid in the protein. To generate the predicted protein structure, the system may repeatedly update an initial (e.g., default) protein structure by adjusting the predicted spatial locations and rotations of the amino acids in the protein structure.

These features and other features are described in more detail below.

Figure 1:
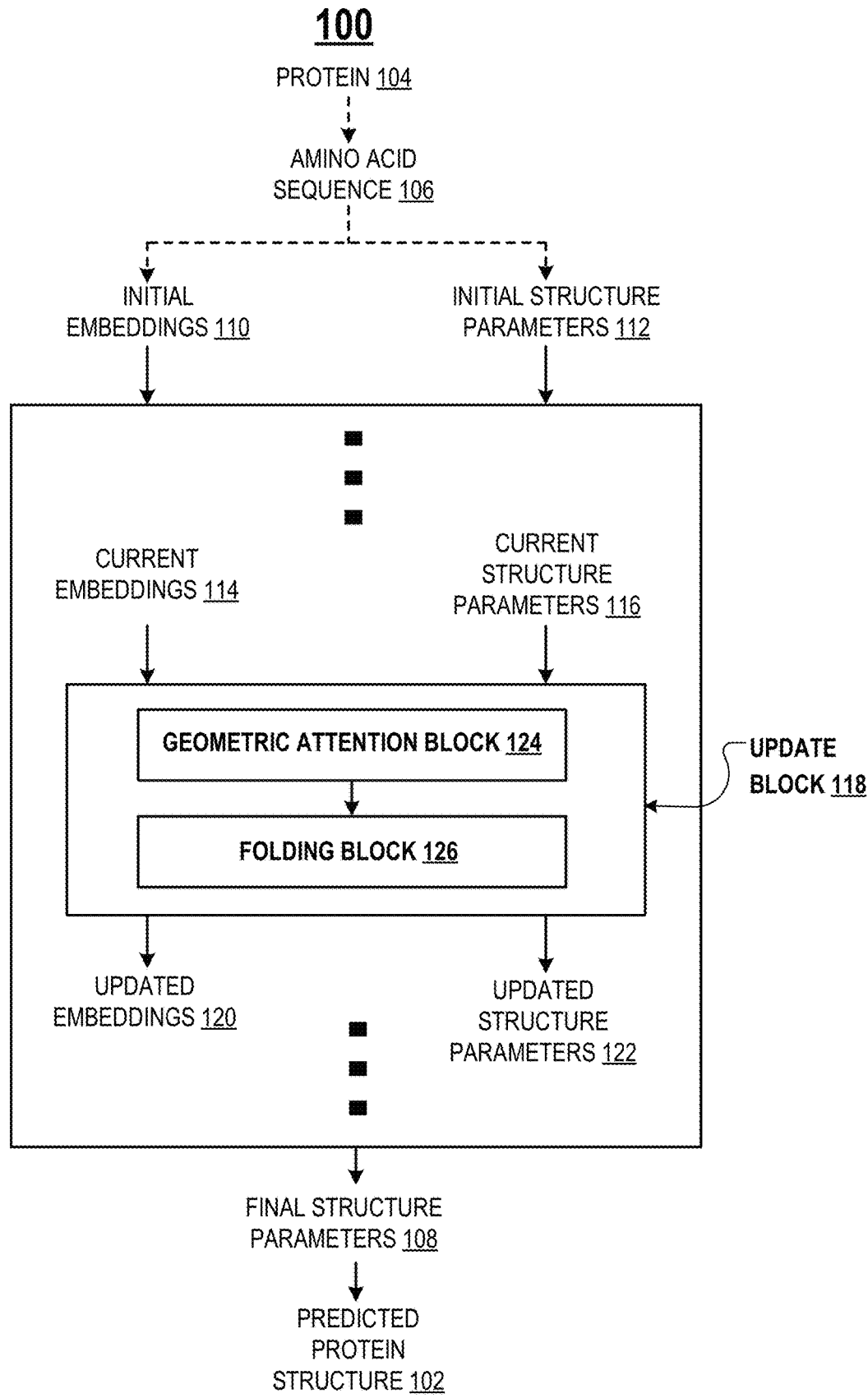
FIG. 1 shows an example protein folding neural network system.

FIG. 1 shows an example protein folding neural network system 100. The protein folding neural network system 100 is an example of a system implemented as computer programs on one or more computers in one or more locations in which the systems, components, and techniques described below are implemented.

The system 100 is configured to generate a predicted structure 102 of the protein 104. Each amino acid in the amino acid sequence 106 of the protein 104 is an organic compound which includes an amino functional group and a carboxyl functional group, as well as a side-chain (i.e., group of atoms) which is specific to the amino acid. The predicted structure 102 defines an estimate of a three-dimensional (3-D) configuration of the atoms in the amino acid sequence 106 of the protein 104 after the protein 104 undergoes protein folding.

As used throughout this specification, the term "protein" may be understood to refer to any biological molecule that is specified by one or more sequences of amino acids. For example, the term protein may be understood to refer to a protein domain (i.e., a portion of an amino acid sequence that can undergo protein folding nearly independently of the rest of the amino acid sequence) or a protein complex (i.e., that is specified by multiple associated amino acid sequences).

The amino acid sequence 106 can be represented in any appropriate numerical format. For example, the amino acid sequence 106 may be represented as a sequence of one-hot vectors. In this example, each one-hot vector represents a corresponding amino acid in the amino acid sequence 106. A one-hot vector has a different component for each different amino acid (e.g., of a predetermined number of amino acids, e.g., 21). A one-hot vector representing a particular amino acid has value one (or some other predetermined value) in the component corresponding to the particular amino acid and value zero (or some other predetermined value) in the other components.

The predicted structure 102 of the protein 104 is defined by the values of a set of structure parameters, in particular, the final structure parameter values 108. The set of structure parameters may include: (i) location parameters, and (ii) rotation parameters, for each amino acid in the protein 104.

The location parameters for an amino acid may specify a predicted 3-D spatial location of a specified atom in the amino acid in the structure of the protein. The specified atom may be the alpha carbon atom in the amino acid, i.e., the carbon atom in the amino acid to which the amino functional group, the carboxyl functional group, and the side-chain are bonded. The location parameters for an amino acid may be represented in any appropriate coordinate system, e.g., a three-dimensional [x, y, z] Cartesian coordinate system.

The rotation parameters for an amino acid may specify the predicted "orientation" of the amino acid in the structure of the protein. More specifically, the rotation parameters may specify a 3-D spatial rotation operation that, if applied to the coordinate system of the location parameters, causes the three "main chain" atoms in the amino acid to assume fixed positions relative to the rotated coordinate system. The three main chain atoms in the amino acid refer to the linked series of alpha carbon, nitrogen, and oxygen atoms in the amino acid. The rotation parameters for an amino acid may be represented, e.g., as an orthonormal 3×3 matrix with determinant equal to 1.

Generally, the location and rotation parameters for an amino acid define an egocentric reference frame for the amino acid. In this reference frame, the side-chain for each amino acid may start at the origin, and the first bond along the side-chain (i.e., the alpha carbon—beta carbon bond) may be along a defined direction.

The folding neural network system 100 receives an input that includes, for each amino acid in the protein: (i) initial values of an embedding 110 for the amino acid, and (ii) initial values of structure parameters 112 for the amino acid. The system 100 processes the input to generate final values of the structure parameters 108 that collectively characterize the predicted structure 102 of the protein.

The initial embeddings 110 of the amino acids of the protein 104 can be generated in any of a variety of ways. In one example, each initial embedding 110 may be a one-hot embedding vector, as described above. Optionally, each one-hot embedding vector may be processed by one or more neural network layers, e.g., convolutional or fully-connected layers. Other ways of generating the initial embeddings 110 are possible.

The structure parameters corresponding to each amino acid may include: (i) location parameters, and (ii) rotation parameters, as described above. The initial structure parameter values 112 may be default values, e.g., where the location parameters for each amino acid are initialized to the origin (e.g., [0,0,0] in a Cartesian coordinate system), and the rotation parameters for each amino acid are initialized to a 3×3 identity matrix.

The system 100 may generate the final structure parameters 108 by repeatedly updating the current values of the embeddings 114 and the structure parameters 116, i.e., starting from their initial values. More specifically, the system 100 includes a sequence of update neural network blocks 118, where each update block 118 is configured to update the current embeddings 114 (i.e., to generate updated embeddings 120) and to update the current structure parameters 116 (i.e., to generate updated structure parameters 122). The system 100 may include other neural network layers or blocks in addition to the update blocks, e.g., that may be interleaved with the update blocks.

Each update block 118 may include: (i) a geometric attention neural network block 124, and (ii) a folding neural network block 126, each of which will be described in more detail next.

The geometric attention block 124 updates the current embeddings using a "geometric" self-attention operation that explicitly reasons about the 3-D geometry of the amino acids in the structure of the protein, i.e., as defined by the structure parameters. More specifically, to update a given embedding, the geometric attention block 124 determines a respective attention weight between the given embedding and each of one or more selected embeddings, where the attention weights depend on both the current embeddings and the current structure parameters. The geometric attention block 124 then updates the given embedding using: (i) the attention weights, (ii) the selected embeddings, and (iii) the current structure parameters.

To determine the attention weights, the geometric attention block 124 processes each current embedding to generate a corresponding "symbolic query" embedding, "symbolic key" embedding, and "symbolic value" embedding. For example, the geometric attention block 124 may generate the symbolic query embedding $q_i$, symbolic key embedding $k_i$, and symbolic value embedding $v_i$ for the i-th amino acid embedding $h_i$ as:

$$q_i = \text{Linear}(h_i) \quad (1)$$

$$k_i = \text{Linear}(h_i) \quad (2)$$

$$v_i = \text{Linear}(h_i) \quad (3)$$

where Linear(•) refers to linear layers having independent learned parameter values.

The geometric attention block 124 additionally processes each current amino acid embedding to generate a corresponding "geometric query" embedding, "geometric key" embedding, and "geometric value" embedding. The geometric query, geometric key, and geometric value embeddings for the amino acid embedding are each 3-D points that are initially generated in the local reference frame of the corresponding amino acid, and then rotated and translated to a global reference frame using the structure parameters for the amino acid. For example, the geometric attention block 124 may generate the geometry query embedding $q_i^p$, geometric key embedding $k_i^p$, and geometric value embedding $y_i^p$ for the i-th amino acid embedding $h_i$ as:

$$q_i^p = R_i \cdot \text{Linear}_p(h_i) + t_i \quad (4)$$

$$k_i^p = R_i \cdot \text{Linear}_p(h_i) + t_i \quad (5)$$

$$v_i^p = R_i \cdot \text{Linear}_p(h_i) + t_i \quad (6)$$

where $\text{Linear}_p(\bullet)$ refers to linear layers having independent learned parameter values that project $h_i$ to a 3-D point (the superscript p indicates that the quantity is a 3-D point), $R_i$ denotes the rotation matrix specified by the rotation parameters for the i-th amino acid, and $t_i$ denotes the location parameters for the i-th amino acid.

To update the embedding $h_i$ corresponding to amino acid i, the geometric attention block 124 may generate attention weights $[a_j]_{j=1}^N$, where N is the total number of amino acids in the protein and $a_j$ is the attention weight between amino acid i and amino acid j, as:

$$[a_j]_{j=1}^N = \text{softmax}\left(\left[\frac{q_i \cdot k_j}{\sqrt{m}} + \alpha |q_i^p - k_j^p|_2^2 + (b_{i,j} \cdot w)\right]_{j=1}^N\right) \quad (7)$$

where $q_i$ denotes the symbolic query embedding for amino acid i, $k_j$ denotes the symbolic key embedding for amino acid j, m denotes the dimensionality of $q_i$ and $k_j$, $\alpha$ denotes a learned parameter, $q_i^p$ denotes the geometric query embedding for amino acid i, $k_j^p$ denotes the geometry key embedding for amino acid j, $|\bullet|_2$ is an $L_2$ norm, and $b_{i,j}$ is an "interaction" vector characterizing a predicted spatial distance between amino acid i and amino acid j in the protein structure (as will be described in more detail next), and w is a learned weight vector.

To generate the interaction vectors $\{b_{i,j}\}_{i,j=1}^N$, the system 100 may process a representation of the protein (e.g., a one-hot embedding of each amino acid in the protein) using a neural network to generate a distance prediction output. The distance prediction output characterizes the predicted distance between each pair of amino acids in the protein structure. In one example, the distance prediction output may specify, for each pair of amino acids in the protein, a probability distribution over a set of possible distance ranges between the pair of amino acids. The set of possible distance ranges may be given by, e.g., {(0,5], (5,10], (10,20], (20, ∞)}, where the distances may be measured in Angstroms (or any other appropriate unit of measure). The system 100 may generate the interaction vectors $\{b_{i,j}\}_{i,j=1}^N$ by processing the distance prediction output using one or more neural network layers, e.g., convolutional neural network layers.

In some implementations, the geometric attention block 124 generate multiple sets of geometric query embeddings, geometric key embeddings, and geometric value embeddings, and uses each generated set of geometric embeddings in determining the attention weights.

After generating the attention weights for the embedding $h_i$ corresponding to amino acid i, the geometric attention block 124 uses the attention weights to update the embedding $h_i$. In particular, the geometric attention block 124 uses the attention weights to generate a "symbolic return" embedding and a "geometric return" embedding, and then updates the embedding using the symbolic return embedding and the geometric return embedding. The geometric attention block 124 may generate the symbolic return embedding $o_i$ for amino acid i, e.g., as:

$$o_i = \sum_j a_j v_j \quad (8)$$

where $[a_j]_{j=1}^N$ denote the attention weights (e.g., defined with reference to equation (7)) and each $v_j$ denotes the symbolic value embedding for amino acid j. The geometric attention block 124 may generate the geometric return embedding $o_i^p$ for amino acid i, e.g., as:

$$o_i^p = R_i^{-1} \cdot \left(\sum_j a_j v_j^p - t_i\right) \quad (9)$$

where the geometric return embedding $o_i^p$ is a 3-D point, $[a_j]_{j=1}^N$ denote the attention weights (e.g., defined with reference to equation (7)), $R_i^{-1}$ is inverse of the rotation matrix specified by the rotation parameters for amino acid i, and $t_i$ are the location parameters for amino acid i. It can be appreciated that the geometric return embedding is initially generated in the global reference frame, and then rotated and translated to the local reference frame of the corresponding amino acid.

The geometric attention block 124 may update the embedding $h_i$ for amino acid i using the corresponding symbolic return embedding $o_i$ (e.g., generated in accordance with equation (8)) and geometric return embedding $o_i^p$ (e.g., generated in accordance with equation (9)), e.g., as:

$$h_i^{next} = \text{LayerNorm}(h_i + \text{Linear}(o_i, o_i^p, |o_i^p|)) \quad (10)$$

where $h_i^{next}$ is the updated embedding for amino acid i, |•| is a norm, e.g., an $L_2$ norm, and LayerNorm(•) denotes a layer normalization operation, e.g., as described with reference to: J. L. Ba, J. R. Kiros, G. E. Hinton, "Layer Normalization," arXiv:1607.06450 (2016).

Updating the embeddings 110 of the amino acids using concrete 3-D geometric embeddings, e.g., as described with reference to equations (4)-(6), enables the geometric attention block 124 to reason about 3-D geometry in updating the embeddings. Moreover, each update block updates the embeddings and the structure parameters in a manner that is invariant to rotations and translations of the overall protein structure. For example, applying the same global rotation and translation operation to the initial structure parameters provided to the system 100 would cause the system 100 to generate a predicted structure that is globally rotated and translated in the same way. Therefore, global rotation and translation operations applied to the initial structure parameters would not affect the accuracy of the predicted protein structure generated by the system 100 starting from the initial structure parameters. The rotational and translational invariance of the representations generated by the system 100 facilitates training, e.g., because the system 100 automatically learns to generalize across all rotations and translations of protein structures.

The updated embeddings for the amino acids may be further transformed by one or more additional neural network layers in the geometric attention block 124, e.g., linear neural network layers, before being provided to the folding block 126.

After the geometric attention block 124 updates the current embeddings 114 for the amino acids, the folding block 126 updates the current structure parameters 116 using the updated embeddings 120. For example, the folding block 126 may update the current location parameters $t_i$ for amino acid i as:

$$t_i^{next} = t_i + \text{Linear}(h_i^{next}) \quad (11)$$

where $t_i^{next}$ are the updated location parameters, Linear(•) denotes a linear neural network layer, and $h_i^{next}$ denotes the updated embedding for amino acid i. In another example, the rotation parameters $R_i$ for amino acid i may specify a rotation matrix, and the folding block 126 may update the current rotation parameters $R_i$ as:

$$w_i = \text{Linear}(h_i) \quad (12)$$

$$R_i^{next} = R_i \cdot \text{QuaternionToRotation}(1+w_i) \quad (13)$$

where $w_i$ is a three-dimensional vector, Linear(•) is a linear neural network layer, $h_i$ is the embedding for amino acid i, $1+w_i$ denotes a quaternion with real part 1 and imaginary part $w_i$, and QuaternionToRotation(•) denotes an operation that transforms a quaternion into an equivalent 3×3 rotation matrix. Updating the rotation parameters using equations (12)-(13) ensures that the updated rotation parameters define a valid rotation matrix, e.g., an orthonormal matrix with determinant one.

The system 100 may provide the updated structure parameters generated by the final update block 118 as the final structure parameters 108 that define the predicted protein structure 102. The system 100 may include any appropriate number of update blocks, e.g., 5 update blocks, 25 update blocks, or 125 update blocks. Optionally, each of the update blocks of the system 100 may share a single set of parameter values that are jointly updated during training of the system 100. Sharing parameter values between the update blocks 118 reduces the number of trainable parameters of the system 100 and may therefore facilitate effective training of the folding neural network, e.g., by stabilizing the training and reducing the likelihood of overfitting.

A training engine may train the system 100 from end-to-end to optimize an objective function referred to herein as a structure loss. The training engine may train the system 100 on a set of training data including multiple training examples. Each training example may specify: (i) a training input initial embeddings and initial structure parameters for the amino acid sequence of a protein, and (ii) a target protein structure that should be generated by the system 100 by processing the training input. Target protein structures used for training the system 100 may be determined using experimental techniques, e.g., x-ray crystallography.

The structure loss may characterize a similarity between: (i) a predicted protein structure generated by the system 100, and (ii) the target protein structure that should have been generated by the system. For example, the structure loss $\mathcal{L}_{structure}$ may be given by:

$$\mathcal{L}_{structure} = \frac{1}{N^2} \sum_{i,j=1}^{N} \left(1 - \frac{|t_{ij} - \widetilde{t_{ij}}|}{A}\right)_+ \quad (14)$$

$$t_{ij} = R_i^{-1}(t_j - t_i) \quad (15)$$

$$\widetilde{t_{ij}} = \widetilde{R}_i^{-1}(\widetilde{t}_j - \widetilde{t}_i) \quad (16)$$

where N is the number of amino acids in the protein, $t_i$ denote the predicted location parameters for amino acid i, $R_i$ denotes a 3×3 rotation matrix specified by the predicted rotation parameters for amino acid i, $\widetilde{t}_i$ are the target location parameters for amino acid i, $\widetilde{R}_i$ denotes a 3×3 rotation matrix specified by the target rotation parameters for amino acid i, A is a constant, $R_i^{-1}$ refers to the inverse of the 3×3 rotation matrix specified by predicted rotation parameters $R_i$, $\widetilde{R}_i^{-1}$ refers to the inverse of the 3×3 rotation matrix specified by the target rotation parameters $\widetilde{R}_i$, and (•)$_+$ denotes a rectified linear unit (ReLU) operation.

The structure loss defined with reference to equations (14)-(16) may be understood as averaging the loss $|t_{ij} - \widetilde{t_{ij}}|$ over each pair of amino acids in the protein. The term $t_{ij}$ defines the predicted spatial location of amino acid j in the predicted frame of reference of amino acid i, and $\widetilde{t_{ij}}$ defines the actual spatial location of amino acid j in the actual frame of reference of amino acid i. These terms are sensitive to the predicted and actual rotations of amino acid i and j, and therefore carry richer information than loss terms that are only sensitive to the predicted and actual distances between amino acids. Optimizing the structure loss encourages the system 100 to generate predicted protein structures that accurately approximate true protein structures.

The training engine may train the structure prediction system 100 on the training data over multiple training iterations, e.g., using stochastic gradient descent training techniques.

Optionally, each update block of the system 100 may be associated with a respective structure loss that characterizes the accuracy of the predicted protein structure defined by the updated structure parameters generated by the update block. During training of the system 100, gradients of the structure loss associated with each update block may be backpropagated through the system 100.

Figure 2:
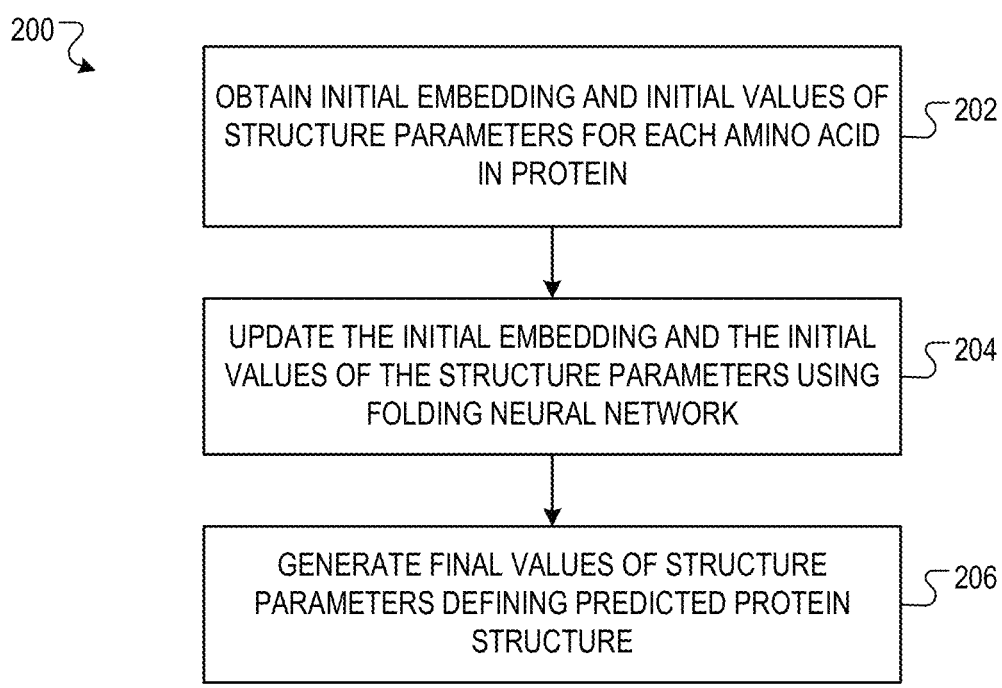
FIG. 2 is a flow diagram of an example process for predicting the structure of a protein.

FIG. 2 is a flow diagram of an example process 200 for predicting the structure of a protein specified by an amino acid sequence. For convenience, the process 200 will be described as being performed by a system of one or more computers located in one or more locations. For example, a protein folding neural network system, e.g., the protein folding neural network system 100 of FIG. 1, appropriately programmed in accordance with this specification, can perform the process 200.

The system obtains an initial embedding and initial values of structure parameters for each amino acid in the amino acid sequence (202). The structure parameters for each amino acid include location parameters that specify a predicted three-dimensional spatial location of the amino acid in the structure of the protein.

The system processes a network input including the initial embedding and the initial values of the structure parameters for each amino acid in the amino acid sequence using a folding neural network (204). The folding neural network includes multiple update blocks, where each update block includes multiple neural network layers. Each update block is configured to: (i) receive an input including a current embedding and current values of the structure parameters for each amino acid, and (ii) process the input to update the current embedding and the current values of the structure parameters for each amino acid.

The system uses the folding neural network to generate a network output that includes final values of the structure parameters for each amino acid in the amino acid sequence (206). The final values of the structure parameters for each amino acid in the amino acid sequence collectively characterize the predicted structure of the protein.

Figure 3:
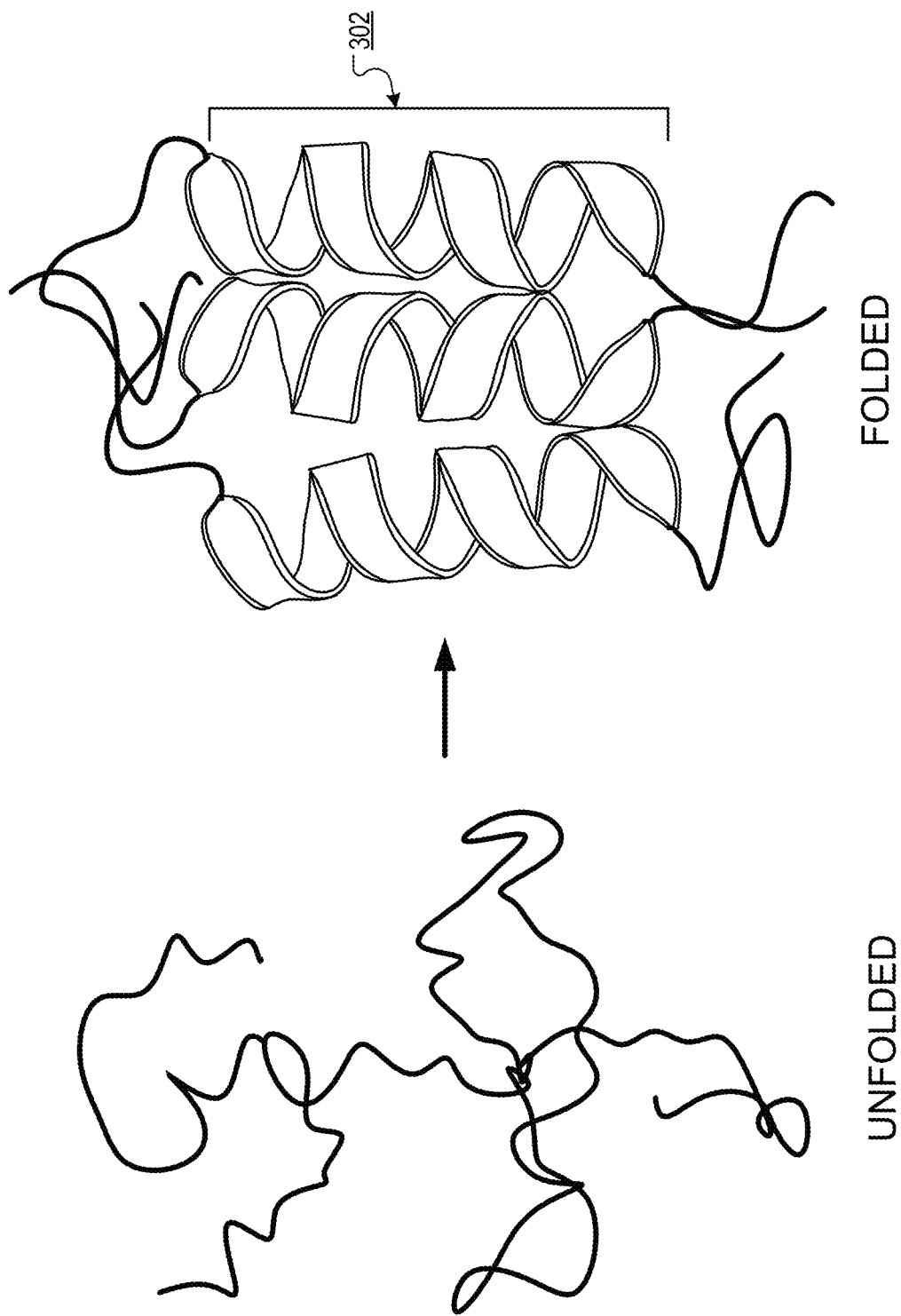
FIG. 3 is an illustration of an unfolded protein and a folded protein.

FIG. 3 is an illustration of an unfolded protein and a folded protein. The unfolded protein is a random coil of amino acids. The unfolded protein undergoes protein folding and folds into a 3D configuration. Protein structures often include stable local folding patterns such alpha helices (e.g., as depicted by 302) and beta sheets.

Figure 4:
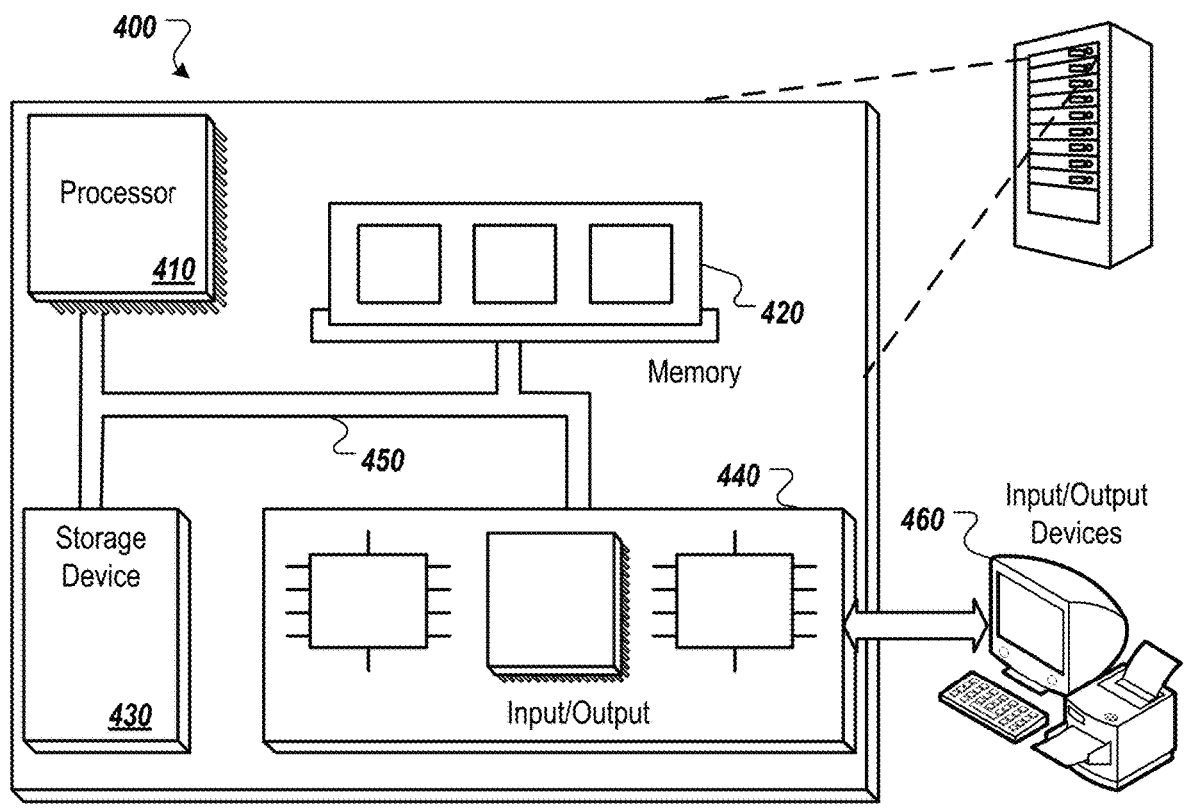
FIG. 4 is a block diagram of an example computing system.

FIG. 4 is block diagram of an example computer system 400 that can be used to perform operations described above. The system 400 includes a processor 410, a memory 420, a storage device 430, and an input/output device 440. Each of the components 410, 420, 430, and 440 can be interconnected, for example, using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 can include, for example, a hard disk device, an optical disk device, a storage device that is shared over a network by multiple computing devices (e.g., a cloud storage device), or some other large capacity storage device.

The input/output device 440 provides input/output operations for the system 400. In one implementation, the input/output device 440 can include one or more network interface devices, e.g., an Ethernet card, a serial communication device, e.g., and RS-232 port, and/or a wireless interface device, e.g., and 802.11 card. In another implementation, the input/output device can include driver devices configured to receive input data and send output data to other input/output devices, e.g., keyboard, printer and display devices 460. Other implementations, however, can also be used, such as mobile computing devices, mobile communication devices, set-top box television client devices, etc.

Although an example processing system has been described in FIG. 4, implementations of the subject matter and the functional operations described in this specification can be implemented in other types of digital electronic circuitry, or in computer software, firmware, or hardware, including the structures disclosed in this specification and their structural equivalents, or in combinations of one or more of them.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:
obtaining an initial embedding and initial values of structure parameters for each amino acid in an amino acid sequence of a protein, wherein the structure parameters for each amino acid comprise location parameters that specify a predicted three-dimensional (3D) spatial location of the amino acid in the structure of the protein;
processing a network input comprising the initial embedding and the initial values of the structure parameters for each amino acid in the amino acid sequence using a folding neural network to generate a network output comprising final values of the structure parameters for each amino acid in the amino acid sequence,
wherein the folding neural network comprises a plurality of update blocks, wherein each update block comprises a plurality of neural network layers and is configured to:
receive an update block input comprising a current embedding and current values of the structure parameters for each amino acid in the amino acid sequence; and
process the update block input to update the current embedding and the current values of the structure parameters for each amino acid in the amino acid sequence, comprising:
updating the current embeddings for the amino acids in the amino acid sequence, comprising applying an attention operation over the current embeddings of the amino acids in the amino acid sequence,
wherein the attention operation over the current embeddings of the amino acids in the amino acid sequence: (i) depends at least in part on a 3D geometry defined by the current values of the structure parameters for the amino acids in the amino acids sequence, and (ii) is invariant to rotations and translations over the 3D geometry defined by the current values of the structure parameters for the amino acids in the amino acid sequence;
wherein the final values of the structure parameters for each amino acid in the amino acid sequence collectively characterize a predicted structure of the protein; and
presenting a 3D visual representation of the predicted structure of the protein on a display of a user device.

2. The method of claim 1, wherein the structure parameters for each amino acid further comprise rotation parameters that specify a predicted spatial orientation of the amino acid in the structure of the protein.

3. The method of claim 2, wherein the rotation parameters define a 3×3 rotation matrix.

4. The method of claim 1, wherein processing the update block input to update the current embedding and the current values of the structure parameters for each amino acid in the amino acid sequence further comprises:
updating the current values of the structure parameters for each amino acid in the amino acid sequence based on the updated embeddings for the amino acids in the amino acid sequence.

5. The method of claim 1, wherein applying the attention operation over the current embeddings of the amino acids in the amino acid sequence comprises:
determining an attention weight for each amino acid in the amino acid sequence, comprising:
generating a three-dimensional query embedding of the given amino acid based on the current embedding of the given amino acid and the current values of the structure parameters for the given amino acid;
generating, for each amino acid in the amino acid sequence, a three-dimensional key embedding of the amino acid based on the current embedding of the amino acid and the current values of the structure parameters for the amino acid; and
determining the attention weight for each amino acid in the amino acid sequence based at least in part on a difference between: (i) the three-dimensional key embedding of the amino acid, and (ii) the three-dimensional query embedding of the given amino acid; and
updating the current embedding of the given amino acid using the attention weights.

6. The method of claim 5, wherein generating the three-dimensional query embedding of the given amino acid based on the current embedding of the given amino acid and the current values of the structure parameters for the given amino acid comprises:
processing the current embedding of the given amino acid using a linear neural network layer that generates a three-dimensional output; and
applying a rotation operation and a translation operation to the three-dimensional output of the linear neural network layer, wherein the rotation operation is specified by current values of rotation parameters for the given amino acid and the translation operation is specified by current values of location parameters for the given amino acid.

7. The method of claim 5, wherein generating a three-dimensional key embedding of an amino acid based on the current embedding of the amino acid and the current values of the structure parameters for the amino acid comprises:
processing the current embedding of the amino acid using a linear neural network layer that generates a three-dimensional output; and
applying a rotation operation and a translation operation to the three-dimensional output of the linear neural network layer, wherein the rotation operation is specified by current values of rotation parameters for the amino acid and the translation operation is specified by current values of location parameters for the amino acid.

8. The method of claim 5, wherein updating the current embedding of the given amino acid using the attention weights comprises:
generating, for each amino acid in the amino acid sequence, a three-dimensional value embedding of the amino acid based on the current embedding of the amino acid;

determining a weighted linear combination of the three-dimensional value embeddings of the amino acids using the attention weights;

generating a geometric return embedding by applying a rotation operation and a translation operation to the weighted linear combination, wherein the rotation operation inverts a rotation operation specified by current values of rotation parameters for the given amino acid and the translation operation is specified by a negative of current values of location parameters for the amino acid; and updating the current embedding of the given amino acid based on the geometric return embedding.

9. The method of claim 5, wherein updating the current values of the structure parameters for each amino acid in the amino acid sequence based on the updated embeddings for the amino acids in the amino acid sequence comprises, for each amino acid:

determining updated values of location parameters for the amino acid as a sum of: (i) current values of the location parameters for the amino acid, and (ii) a linear projection of the updated embedding of the amino acid;

determining updated values of rotation parameters for the amino acid as a composition of: (i) a rotation operation specified by current values of the rotation parameters for the amino acid, and (ii) a rotation operation specified by a quaternion with real part 1 and imaginary part specified by a linear projection of the updated embedding of the amino acid.

10. The method of claim 5, further comprising determining the attention weights for the amino acids in the amino acid sequence based data characterizing predicted distances between pairs of amino acids in the structure of the protein.

11. The method of claim 10, wherein the data characterizing predicted distances between pairs of amino acids in the structure of the protein comprises, for each pair of amino acids, a probability distribution over a set of possible distance ranges between the pair of amino acids.

12. A system comprising:
one or more computers; and
one or more storage devices communicatively coupled to the one or more computers, wherein the one or more storage devices store instructions that, when executed by the one or more computers, cause the one or more computers to perform operations comprising:
obtaining an initial embedding and initial values of structure parameters for each amino acid in an amino acid sequence of a protein, wherein the structure parameters for each amino acid comprise location parameters that specify a predicted three-dimensional (3D) spatial location of the amino acid in the structure of the protein;
processing a network input comprising the initial embedding and the initial values of the structure parameters for each amino acid in the amino acid sequence using a folding neural network to generate a network output comprising final values of the structure parameters for each amino acid in the amino acid sequence,
wherein the folding neural network comprises a plurality of update blocks, wherein each update block comprises a plurality of neural network layers and is configured to:
receive an update block input comprising a current embedding and current values of the structure parameters for each amino acid in the amino acid sequence; and
process the update block input to update the current embedding and the current values of the structure parameters for each amino acid in the amino acid sequence, comprising:
updating the current embeddings for the amino acids in the amino acid sequence, comprising applying an attention operation over the current embeddings of the amino acids in the amino acid sequence,
wherein the attention operation over the current embeddings of the amino acids in the amino acid sequence: (i) depends at least in part on a 3D geometry defined by the current values of the structure parameters for the amino acids in the amino acids sequence, and (ii) is invariant to rotations and translations over the 3D geometry defined by the current values of the structure parameters for the amino acids in the amino acid sequence;
wherein the final values of the structure parameters for each amino acid in the amino acid sequence collectively characterize a predicted structure of the protein; and
presenting a 3D visual representation of the predicted structure of the protein on a display of a user device.

13. The system of claim 12, wherein the structure parameters for each amino acid further comprise rotation parameters that specify a predicted spatial orientation of the amino acid in the structure of the protein.

14. The system of claim 13, wherein the rotation parameters define a 3×3 rotation matrix.

15. The system of claim 12, wherein processing the update block input to update the current embedding and the current values of the structure parameters for each amino acid in the amino acid sequence further comprises:
updating the current values of the structure parameters for each amino acid in the amino acid sequence based on the updated embeddings for the amino acids in the amino acid sequence.

16. The system of claim 12, wherein applying the attention operation over the current embeddings of the amino acids in the amino acid sequence comprises:
determining an attention weight for each amino acid in the amino acid sequence, comprising:
generating a three-dimensional query embedding of the given amino acid based on the current embedding of the given amino acid and the current values of the structure parameters for the given amino acid;
generating, for each amino acid in the amino acid sequence, a three-dimensional key embedding of the amino acid based on the current embedding of the amino acid and the current values of the structure parameters for the amino acid; and
determining the attention weight for each amino acid in the amino acid sequence based at least in part on a difference between: (i) the three-dimensional key embedding of the amino acid, and (ii) the three-dimensional query embedding of the given amino acid; and
updating the current embedding of the given amino acid using the attention weights.

17. One or more non-transitory computer storage media storing instructions that when executed by one or more computers cause the one or more computers to perform operations comprising:
obtaining an initial embedding and initial values of structure parameters for each amino acid in an amino acid sequence of a protein, wherein the structure parameters for each amino acid comprise location parameters that specify a predicted three-dimensional (3D) spatial location of the amino acid in the structure of the protein;

processing a network input comprising the initial embedding and the initial values of the structure parameters for each amino acid in the amino acid sequence using a folding neural network to generate a network output comprising final values of the structure parameters for each amino acid in the amino acid sequence, wherein the folding neural network comprises a plurality of update blocks, wherein each update block comprises a plurality of neural network layers and is configured to:

receive an update block input comprising a current embedding and current values of the structure parameters for each amino acid in the amino acid sequence; and process the update block input to update the current embedding and the current values of the structure parameters for each amino acid in the amino acid sequence, comprising:

updating the current embeddings for the amino acids in the amino acid sequence, comprising applying an attention operation over the current embeddings of the amino acids in the amino acid sequence, wherein the attention operation over the current embeddings of the amino acids in the amino acid sequence: (i) depends at least in part on a 3D geometry defined by the current values of the structure parameters for the amino acids in the amino acids sequence, and (ii) is invariant to rotations and translations over the 3D geometry defined by the current values of the structure parameters for the amino acids in the amino acid sequence;

wherein the final values of the structure parameters for each amino acid in the amino acid sequence collectively characterize a predicted structure of the protein; and presenting a 3D visual representation of the predicted structure of the protein on a display of a user device.

18. The non-transitory computer storage media of claim 17, wherein the structure parameters for each amino acid further comprise rotation parameters that specify a predicted spatial orientation of the amino acid in the structure of the protein.

19. The non-transitory computer storage media of claim 18, wherein the rotation parameters define a 3×3 rotation matrix.

20. The non-transitory computer storage media of claim 17, wherein processing the update block input to update the current embedding and the current values of the structure parameters for each amino acid in the amino acid sequence comprises:

wherein processing the update block input to update the current embedding and the current values of the structure parameters for each amino acid in the amino acid sequence further comprises:

updating the current values of the structure parameters for each amino acid in the amino acid sequence based on the updated embeddings for the amino acids in the amino acid sequence.

* * * * *